US007632482B1

(12) United States Patent
Insepov et al.

(10) Patent No.: US 7,632,482 B1
(45) Date of Patent: Dec. 15, 2009

(54) METHOD FOR NANO-PUMPING USING CARBON NANOTUBES

(75) Inventors: Zeke Insepov, Darien, IL (US); Ahmed Hassanein, Bolingbrook, IL (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 359 days.

(21) Appl. No.: 11/566,362

(22) Filed: Dec. 4, 2006

(51) Int. Cl.
*D01F 9/12* (2006.01)
(52) U.S. Cl. .................. 423/447.1; 977/742; 977/752
(58) Field of Classification Search ............ 977/742, 977/752; 423/447
See application file for complete search history.

(56) References Cited

U.S. PATENT DOCUMENTS

2003/0021694 A1* 1/2003 Yevin .................... 417/53

OTHER PUBLICATIONS

Yoon et al, Sound Wave Propagation, Jour App Phy, 2003, 93, 8, 4801-4806.*
Insepov et al, Nanopumping, Nano Letters, 2006, 6, 9, 1893-1895.*

* cited by examiner

*Primary Examiner*—Melvin C Mayes
*Assistant Examiner*—Bijay S Saha
(74) *Attorney, Agent, or Firm*—Mark C. Lang; Brian J. Lally; Paul A. Gottlieb

(57) ABSTRACT

The present invention relates generally to the field of nanotechnology, carbon nanotubes and, more specifically, to a method and system for nano-pumping media through carbon nanotubes. One preferred embodiment of the invention generally comprises: method for nano-pumping, comprising the following steps: providing one or more media; providing one or more carbon nanotubes, the one or more nanotubes having a first end and a second end, wherein said first end of one or more nanotubes is in contact with the media; and creating surface waves on the carbon nanotubes, wherein at least a portion of the media is pumped through the nanotube.

29 Claims, 3 Drawing Sheets

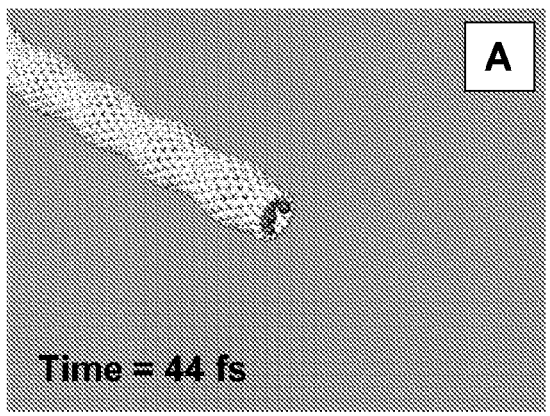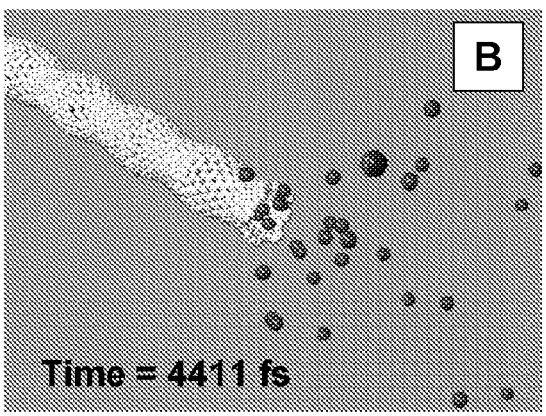
FIG. 1A  FIG. 1B
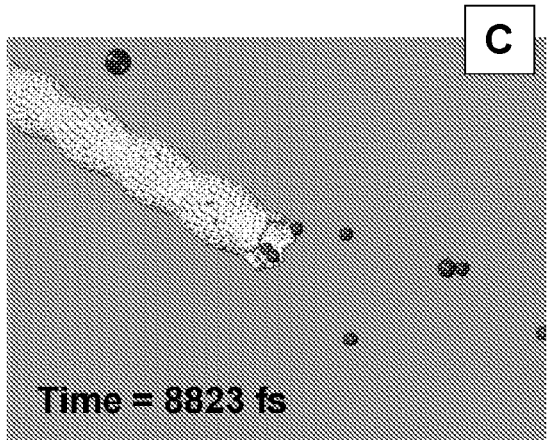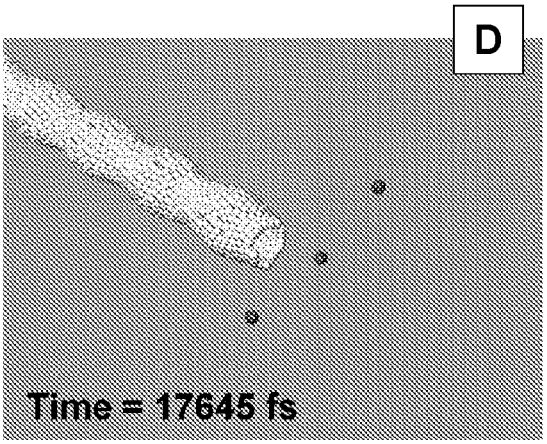
FIG. 1C  FIG. 1D

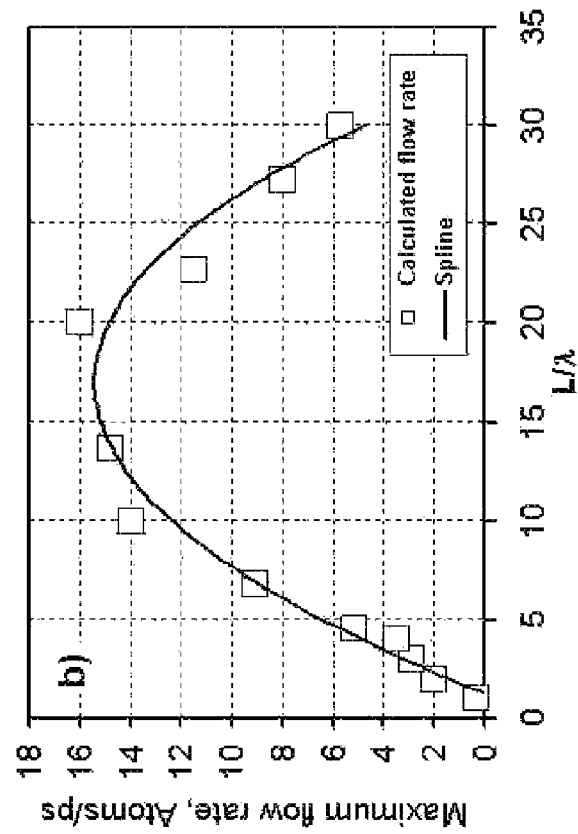
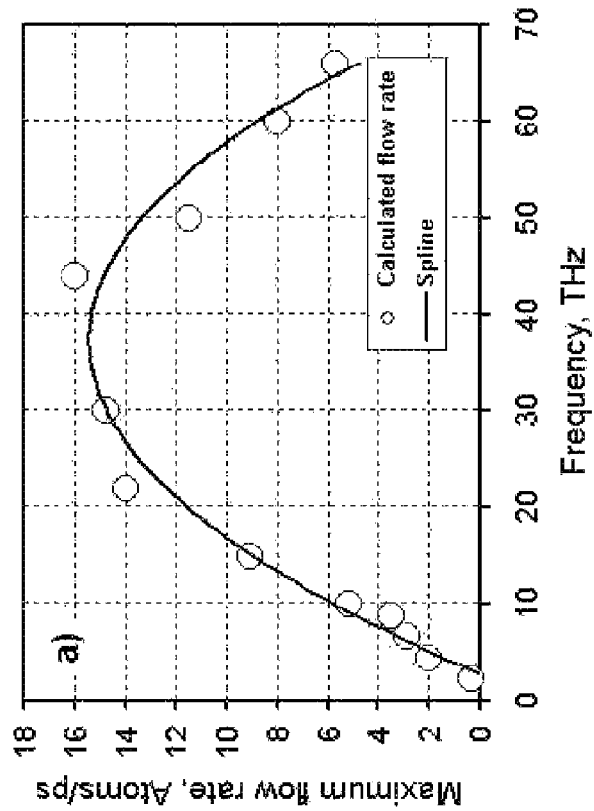
FIG. 3B
FIG. 3A

METHOD FOR NANO-PUMPING USING CARBON NANOTUBES

STATEMENT OF GOVERNMENTAL SUPPORT

This invention was made during work supported by the U.S. Department of Energy under Contract No. W-31-109-ENG-38. Therefore, the United States Government has certain rights to this invention.

FIELD OF INVENTION

The present invention relates generally to the field of nanotechnology, carbon nanotubes and, more specifically, to a method and system for nano-pumping media through carbon nanotubes.

BACKGROUND OF INVENTION

The study of narrow channels has become a popular area of research since the discovery of carbon nanotubes by Sumio Ijima in 1991. Ijima found that carbon fibers, which were already known to exist, were in fact hollow. Part of the fullerene structural family (which also includes buckyballs), carbon nanotubes can be generally described as rolled-up sheets of graphite with diameters on the order of several nanometers (1 nm=$10^{-9}$ m). There are two common types of carbon nanotubes: single-walled carbon nanotubes and multi-walled carbon nanotubes. Single-walled carbon nanotubes consist of one rolled sheet of one-atom-thick graphite (called graphene). Multi-walled carbon nanotubes are made of concentric cylinders of graphene (e.g., a single-walled carbon nanotube within a larger single-walled carbon nanotube). Despite their small size, carbon nanotubes are known to exhibit remarkable strength and have other unexpected electrical and structural properties.

In recent years the study of fluid control in narrow channels has become a hot area of research. Current research has centered on microflow systems including liquid flows in narrow slit-pores, very thin liquid film on solid surfaces, flows in micropumps, microarrays and membranes. Although fluid flow dynamics in carbon nanotubes has been studied to some degree, research in this area has focused on: laser driven atomic transport using electric current which drives ions using drag forces (citation) and nano-pipette systems for dragging metal ions through a multi-walled CNT using electromigration forces. There is a need in the art for a new method of pumping non-ionic media on a nanoscale.

Nanotubes have also been studied for their energy storage capabilities. Of particular importance is the issue of how to store and release hydrogen in a safe and practical manner. The energy storage capabilities of carbon nanotubes have been explored through the two forms of adsorption: chemisorption and physisorption. Adsorption, in general, is where a gas or liquid accumulates on the surface of a solid or liquid and forms a molecular or atomic film. Chemisorption is a form of adsorption where molecules attach to the surface of the carbon nanotube by forming a chemical bond. Physisorption is a form of adsorption where molecules adhere to the surface of the carbon nanotube only by weak intermolecular forces (Van der Waals forces). However, the chemisorption and physisorption methods of hydrogen storage are problematic because the release of hydrogen from the carbon nanotube structure is complicated. Proposed methods to release hydrogen from the carbon nanotube structure require very high temperatures and are thus unrealistic in application. There is a need in the art for a new hydrogen storage and release method and system.

A new method for storing and pumping media on a nanoscale could have a significant effect on a wide range of technologies including but not limited to: hydrogen energetics, nano-robotics, nano-scale printing, atom optics, quantum computing, semiconductors, forensic and nucleotide analysis, chemical process control, cell biology, medical drug delivery, and molecular medicine.

BRIEF SUMMARY OF THE INVENTION

The present invention is a method for nano-pumping gaseous, liquid solid, or other media through carbon nanotubes. One embodiment of the invention generally comprises the following steps: (1) providing a plurality of carbon nanotubes, each carbon nanotube having a first and second end with the first end in contact with a gaseous, liquid, or solid media; and (2) creating surface waves along the carbon nanotubes which pumps media through the tube(s).

In an alternative embodiment, the carbon nanotubes are filled (imbibition) before surface waves are created on the carbon nanotubes.

BRIEF DESCRIPTION OF THE DRAWINGS

FIGS. 1A-1D illustrate the Molecular Dynamics simulation described below.

FIGS. 3A-3B are graphs displaying the frequency-dependence of the flow rate of the media through the carbon nanotube.

DETAILED DESCRIPTION OF THE INVENTION

Figures 2A, 2B:
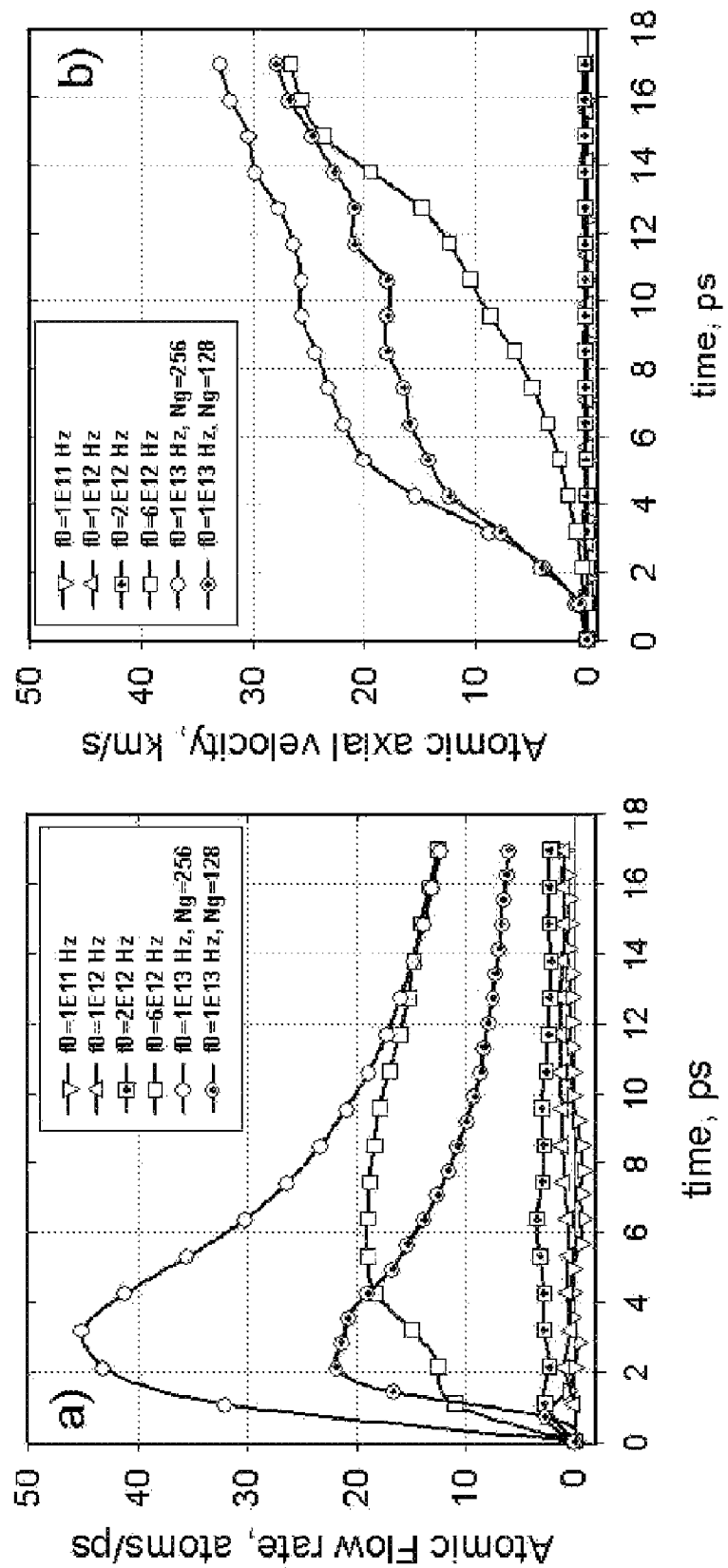
FIGS. 2A-2B are graphs displaying the time-dependence of the flow rate of the media through the carbon nanotube.

The present invention relates to a method for nano-pumping media through carbon nanotubes. More specifically, the present invention relates to a method of carbon nanotube-pumping in which waves are produced at the surface of the nanotube(s) to propagate liquid, gases, or other media through the nanotube(s).

One preferred embodiment of the invented method of nano-pumping generally comprises the following steps:
a. providing a media to be pumped;
b. providing a plurality of carbon nanotubes, each carbon nanotube having a first and second end with the first end in contact with said media;
c. creating surface waves along the carbon nanotubes.

The surface waves transform the nanotubes into a nanoscale pump capable of pumping media. The driving force behind the nano-pump is the friction between the media (i.e. gas, liquid) and the nanotube walls. As shown in FIGS. 1A-D gas atoms inside the carbon nanotube move almost freely along ballistic trajectories when surface waves are created on the nanotubes. The gas atoms are easily accelerated to a very high axial velocity along the direction of the traveling wave. The increase in acceleration is a result of multiple synchronous collisions with the moving nanotube walls (resulting from the surface waves). The surface waves cause the media to be pumped through the nanotube in the direction of the traveling surface wave.

As noted in an alternate embodiment the nanotubes can be imbibed with media prior to the creation of surface waves on the nanotube(s).

Media

The media pumped through the nanotube can be virtually any media capable of being pumped through the chosen nanotubes. Preferably the media will have atoms being smaller than the diameter of the nanotube, preferably having a size of lest than ½ the diameter of the nanotube, even more preferably less than or equal to a carbon atom diameter. The media can be a gas, liquid, solid, other media, or combinations thereof.

In one preferred embodiment the media is comprised of atoms having individual masses less than that of a carbon atom, more preferably the media is comprised of hydrogen or helium gas, and even more preferably hydrogen gas.

The nanotubes can be imbibed with the media prior/during pumping or the media can be drawn into the nanotube by a vacuum-like effect caused by the surface waves.

Nanotubes

The nanotubes used in the present invention are carbon nanotubes. Depending on the application, carbon nanotubes may be needed in different diameters, lengths and configurations. The carbon nanotubes (CN) can be produced the using techniques well-known in the art (e.g., U.S. Pat. No. 6,900, 580, U.S. Pat. No. 6,939,525, U.S. Pat. No. 7,008,605) or purchased from a manufacturer. Several manufacturers of carbon nanotubes that may be suited for the present invention are: NanoLab, Inc., Newton, Mass.; Cheap Tubes, Inc., Brattleboro, Vt.; and Helix Material Solutions, Richardson, TX. All three of these manufacturers are able to produce carbon nanotubes in various sizes and arrangements. When possible one may purchase carbon nanotubes prefilled with a desired media.

In terms of size, there are several factors to consider in the context of the present invention. The carbon nanotubes used in the present invention can have a wide range of diameters. However, it is preferable to employ carbon nanotubes having diameters between about 1 and 10 nm. The diameters of nanotube are limited to the strength of the tube as the nanotubes with large diameters are not normally strong enough to be considered as a future nanopump media.

The length of the carbon nanotubes can be varied, however, as discussed below, the length of the nanotube may affect the preferred frequencies of the waves. The carbon nanotubes may be any length, but the length will usually be dictated by the application for which the carbon nanotubes will be used A suitable range for the length of the nanotube is between about 10 nm-1000 nm, preferably between about 10 nm and 100 nanometers. The length of the nanotube defines the resonant frequency of the nanopump. If the length is too large, e.g. larger than a few mm, it will be very difficult to stabilize the nanotube for using it as a nanopump. The nanopump effect may not be exist at such long nanotube Therefore, we limit the overall length for a stable nanopumping effect to a few hundred microns.

For larger diameters, the carbon nanotubes may preferably be multi-walled carbon nanotubes as multi-walled carbon nanotubes tend to be more structurally stable.

Another characteristic of carbon nanotubes, the chiral vector, need not be any specific pair of indices. The chiral vector (n, m) of a carbon nanotube represents the way in which the graphene sheet is rolled to form the carbon nanotube. There are three types of chiral vectors: zigzag (if either n=0 or m=0 and the chiral angle is 0°), armchair (if n=m, and the chiral angle is 30), and chiral (all other vectors with chiral angle between 0° and 30°). In the present invention, the chiral vector, sometimes also referred to as simply "chirality," does not appear to affect the method and, therefore, can have any value.

In terms of arrangement, carbon nanotubes can be made or purchased in a variety of configurations including but not limited to: bundles, ropes, or arrays. A bundle of carbon nanotubes generally describes a grouping, in some fashion, of more than one carbon nanotube. Bundles of carbon nanotubes can be aligned carbon nanotubes (e.g., carbon nanotube ropes) or carbon nanotubes arranged in a random configuration (e.g., crisscrossed in a straw-like mat). Ropes are bundles of carbon nanotubes that are packed together parallel to one another in an orderly fashion. Carbon nanotubes naturally form ropes and are held in such a formation by Van der Waals forces (weak intermolecular forces). Arrays are groupings of carbon nanotubes where the carbon nanotubes have been grown in a particular formation (usually not touching one other) to serve a particular purpose. For example, a 5 carbon nanotube by 5 carbon nanotube square array where there is 5 nm of space between all carbon nanotubes. In arrays, the carbon nanotubes are typically grown on a substrate to which they are then attached at one end.

The present invention is applicable to a single carbon nanotube; however, it can be applied to a plurality of nanotubes. A plurality of nanotubes will have similar nano-pumping effects. The number of nanotubes required will be determined by the specific application. For example, a larger quantity of carbon nanotubes may be required for a hydrogen storage application than for a more exact application, such as medical drug delivery or nano-robotics. Carbon nanotubes also have the option of being filled (imbibition) with a media.

Typically, carbon nanotubes are capped at each end with half of a fullerene (buckyball). However, it is also possible for carbon nanotubes to be open at both ends or capped on just one end. Depending on the application, the carbon nanotube might have any of the above characteristics/configurations.

Surface Waves on Carbon Nanotubes

A salient aspect of the invention is the creation of surface waves on the surface of the nanotubes. The surface waves are preferably transverse longitudinal waves. The waves are more preferably Raleigh waves.

There at least two known methods of creating surface waves on carbon nanotubes. One method uses short laser pulses to generate thermo-acoustic waves on carbon nanotubes as described by K. L. Telschow, V. A. Deason, D. L. Cottle, J. D. Larson III, UHF Acoustic Microscopic Imaging of Resonator Motion, *IEEE* 2000 *Ultrasonics Symposium in Puerto Rico*, Oct. 22-25, 2000, which is hereby incorporated by reference in its entirety.

Another way is to send ultra-sound waves through a liquid or dense gaseous media to carbon nanotubes as described by I. A. Viktorov, *Rayleigh and Lamb Waves: Physical Theory and Applications* (Plenum, New York, 1967), which is hereby incorporated by reference in its entirety.

Both techniques use traveling waves to activate Rayleigh transverse surface waves on the surface of carbon nanotubes. See, J. Yoon et al, Sound Wave Propagation in Multi-Wall Carbon Nanotubes, J. Appl. Phys., Vol. 93, No. 8, 2003; Q. Wang, Wave propagation in carbon nanotubes via nonlocal continuum mechanics, J. Appl. Phys., Vol. 98, 124301, 2005; T. Natsuki et al., Wave propagation of carbon nanotubes embedded in an elastic medium, J. App. Phys. Vol. 97, 044307, 2005; V. N. Popov et al, Elastic properties of single-walled carbon nanotubes, Physical Review B. Vol. 61, No. 4, 2000; all of which are hereby incorporated by reference in their entireties. Whatever technique is used it should be used to a sufficient degree to induce surface waves on the nanotubes of the wave type and frequency described herein.

The induced surface waves can have a wide range of frequencies. The preferred frequency is dependent on the length of the carbon nanotubes being used as discussed in detail below. For shorter carbon nanotubes, the preferred range is generally less than about 60 THz, and more preferably between about 10 and 60 THz. However, for longer carbon nanotubes the frequency could be much smaller.

Rayleigh transverse surface waves are activated when a longitudinal wave traveling in a liquid or gas impinges on a solid surface at an incident angle equal to the Rayleigh angle θ (where θ=Arcsin ($C_p/C_s$), $C_p$ is the velocity of the incident wave and $C_s$ is the velocity of the surface wave in the material). See Viktorov, supra.

The surface waves transform the nanotubes into nano-scale pumps capable of pumping the media. The driving force behind the nano-pump is the friction between the media (i.e. gas, liquid) and the nanotube walls which pumps and/or flows the media in the direction of the traveling surface wave. As shown in FIGS. 1A-D gas atoms inside the carbon nanotube move almost freely along ballistic trajectories when surface waves are created on the nanotubes. The gas atoms are easily accelerated to a very high axial velocity along the direction of the traveling wave. The increase in acceleration is a result of multiple synchronous collisions with the moving nanotube walls (resulting from the surface waves).

Imbibition of Carbon Nanotubes

The carbon nanotubes can be imbibed with one or more media prior to the commencement of the nanopumping process. Such imbibition might be preferable when using the invented method for certain applications including but not limited to: storage uses and delivery methods. For example, the nanotubes could be imbibed with a biologically active compound such as a pharmaceutical or an energy media such as hydrogen, and then released using the invented nanopumping process.

Imbibition is the term used to describe a process for filling carbon nanotubes. One imbibition method is taught by Supple et al., which is hereby incorporated by reference in its entirety. (See, S. Supple and N. Quirke, Rapid Imbibition of Fluids in Carbon Nanotubes, *Phys. Rev. Lett.* 90, 214501 (2003), see, also P. M. Ajayan, S. Iijima, "Capillarity-induced filling of carbon nanotubes". Nature 361, 333-334 (1993); E. Dujardin, T. W. Ebbesen, H. Hiura, K. Tanigaki, "Capillarity and wetting of carbon nanotubes". Science 265, 1850-1852 (1994); M. R. Pederson, J. Q. Broughton, "Nanocapillarity in fullerene tubules". Phys. Rev. Lett. 69, 2689-2692 (1992); B. C. Regan, S. Alon, R. O. Ritchie, U. Dahmen, A. Zettl, "Carbon nanotubes as nanoscale mass conveyors", *Nature* 428, 924-927 (29 Apr. 2004) which are also incorporated by reference in their entireties.

Results

Several simulations were performed using Molecular Dynamics (MD), a type of molecular modeling based on molecular mechanics. The input structure used for the MD simulations came from coordinates of the zigzag nanotube carbon atoms that were generated.

Tersoff and Brenner interaction potentials were used to describe the carbon-carbon interactions of the nanotube. The Tersoff potential is a three-body potential function explicitly including an angular contribution to force that is widely used in MD for silicon, carbon and others. J. Tersoff, Empirical Interatomic Potential for Carbon, With Applications to Amorphous Carbon, *Phys. Rev. Lett.* 61, 2879-2882 (1988); J. Tersoff, New Empirical Approach for the Structure and Energy of Covalent Systems, *Phys. Rev. B* 37, 6991-7000 (1988). The Brenner potential is similar to the Tersoff potential but also includes special parameterizations for carbon and hydrocarbon systems. D. Brenner, Empirical Potential for Hydrocarbons for Use in Simulating the Chemical Vapor Deposition of Diamond Films, *Phys. Rev. B* 42, 9458-9471 (1990).

The overall system was brought into equilibrium at room temperature and Rayleigh transverse surface waves were created by sending traveling waves with a frequency between about $10^6$-$10^{13}$ Hz along the carbon nanotube. The Rayleigh surface waves had a phase velocity of about 22 km/s. Displacement of the carbon in the nanotubes was perpendicular to the axial direction of wave propagation. In other words, the nanotube vibrations were in the radial directions with amplitudes in the interval of 1-5% of the nanotube radii.

Gas atoms in quantities of either 128 or 256 atoms were placed inside the carbon nanotube by applying a traveling wave along the nanotube surface. Four types of gas atoms were used, all with smaller masses than carbon. The MD simulation takes into account the interaction between the gas atoms and the carbon nanotube and how that interaction affects gas flow. The following carbon nanotube chiralities were tested: (5x0), (15x0), (10x0), and (15x15). The total length of the carbon nanotube was equal to 100 Å(10 nm) and the diameter was between 10 to 20 Å(1-2 nm). Depending on the number of gas atoms inside the carbon nanotube, the real simulation time was about 35 ps.

The simulation results in FIGS. 1A-1D show that the gas atoms inside the carbon nanotube move almost freely along ballistic trajectories. Also, the gas atoms are easily accelerated to a very high axial velocity along the direction of the traveling wave. The increase in acceleration is a result of multiple synchronous collisions with the moving nanotube walls (result of the surface waves). Specifically, FIGS. 1A-1D demonstrate the nano-pumping effect for 256 He (helium) atoms (shown by the dark grey small spheres) that were placed inside a carbon nanotube with a length of 100 Å(10 nm) and a diameter of 12 Å(1.2 nm). The carbon nanotube has a chirality of (15x0) and is made of 1410 carbon atoms. After the surface traveling was activated with a frequency of 10 THz and phase velocity of 22 km/s, the helium atoms began to move in the direction of the wave propagation (from left to right as in FIGS. 1A-1D). FIGS. 1A-1D display various instants in time during the simulation and the corresponding positions of the He atoms.

Length/Frequency

During the MD simulations it was discovered that there was relationship between the length of the nanotubes and preferred frequency of the surface waves. During the MD simulations described above atomic fluxes were generated from the nano-pumping effect for various frequencies of the surface waves for the gases initially at rest (velocity of zero) are shown in FIG. 2A. The total flux increases and then, after a few picoseconds, decreases because of the depletion of the gas atoms inside the nanotube.

The average axial velocities of helium atoms are shown in FIG. 2B for various wave frequencies. At about 1 THz, the velocity (flow rate) is rather small. However, at 6 THz, the velocity reaches a hyper-thermal value of about 30 km/s (kinetic energy of the atoms is greater than the thermal energy, $k_BT$).

The frequency dependence of the flow rate is illustrated in FIG. 3A and depends on the total length of the carbon nanotube. In this particular simulation, the nanotube length was chosen to be 100 Å(10 nm) and, therefore, the characteristic frequency of the surface wave is very high. The maximum nano-pumping effect (flow rate) is seen at approximately 38 THz. The maximum flow rates (and axial velocities) for a particular nanotube will occur at different frequencies which depend upon the length of the nanotube.

FIG. 3B shows the dependence of the nano-pumping effect (flow rate) on the ratio of L/λ, where L is the nanotube length and λ is the wavelength of the surface wave. Thus a preferred frequency range for a particular nanotube will be dependent upon the nanotubes length. Preferably the ratio between the L and frequency will be between about 2 and 32, more preferably between about 10 and 25

EXAMPLES

The invented nano-pumping method can be used in a myriad of applications ranging from medicine to energy storage. For example, one embodiment of the invention relates to a method of drug delivery, the carbon nanotubes could be filled with a medicine and attached to a substrate. The carbon nanotube device could then be implanted in the body. The medicine could then be released from the carbon nanotubes by the application, locally, of ultrasound or short laser pulses by a source present on the carbon nanotube device. Alternatively, the ultrasound or short laser pulses could be applied externally to the body in the location where the carbon nanotube device has been implanted. The ultrasound or short laser pulses would cause the medicine to be nano-pumped out of the carbon nanotube. This application could allow for precision drug delivery in the treatment of, for example, cancerous tumors.

Yet another embodiment of the invention relates to the use of nano-pumping for hydrogen storage. The present invention could provide an efficient means for storing and subsequently releasing hydrogen for use in fuel cells and other uses.

Another embodiment relates to the use of nano-pumping in nano-robotics to provide a means for movement of nano-robots by providing a nano-hydraulics system Having described the basic concept of the invention, it will be apparent to those skilled in the art that the foregoing detailed disclosure is intended to be presented by way of example only, and is not limiting. Various alterations, improvements, and modifications are intended to be suggested and are within the scope and spirit of the present invention. Additionally, the recited order of the elements or sequences, or the use of numbers, letters or other designations therefore, is not intended to limit the claimed processes to any order except as may be specified in the claims. All ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as up to, at least, greater than, less than, and the like refer to ranges which can be subsequently broken down into sub-ranges as discussed above. Accordingly, the invention is limited only by the following claims and equivalents thereto. The invention can be applied and adapted to presently known and future developed methods and system.

All publications and patent documents cited in this application are incorporated by reference in their entirety for all purposes to the same extent as if each individual publication or patent document were so individually denoted.

What is claimed is:

1. A method for nano-pumping, comprising the following steps:
   providing one or more media;
   providing one or more carbon nanotubes, the one or more nanotubes having a first end and a second end, wherein said first end of the one or more nanotubes is in contact with the one or more media; and
   creating surface waves on the carbon nanotubes,
   wherein at least a portion of the media is pumped through the nanotube,
   wherein the one or more nanotubes have a defined length L, the surface wave has a defined frequency λ and wherein the ratio between L/λ is between about 2 and 32.

2. The method of claim 1, wherein the one or more media is a liquid, solid, gas or combination thereof.

3. The method of claim 1, wherein the surface waves are Rayleigh transverse surface waves.

4. The method of claim 1, wherein the surface waves have a frequency less than about 60 THz.

5. The method of claim 1, wherein the surface waves have a frequency between about 10 and 60 THz.

6. The method of claim 1, wherein the surface waves are created by sending ultrasound waves to the carbon nanotubes.

7. A method for nano-pumping, comprising the following steps:
   providing one or more media, wherein the media is hydrogen;
   providing one or more carbon nanotubes, the one or more nanotubes having a first end and a second end, wherein said first end of the one or more nanotubes is in contact with the one or more media; and
   creating surface waves on the carbon nanotubes,
   wherein at least a portion of the media is pumped through the nanotube.

8. The method of claim 1, wherein the media is non-ionic.

9. The method of claim 1, wherein the maximum atomic flow rate of the media is between about 5 and 45 atoms/ps.

10. The method of claim 1, wherein the length of the one or more nanotubes is between about 10 nm and 100 nm.

11. The method of claim 1, wherein the maximum atomic axial velocity of the media is between about 2 and 35 km/s.

12. The method of claim 7, wherein the one or more nanotubes have a defined length L, the surface wave has a defined frequency λ and wherein the ratio between L/λ is between about 2 and 32.

13. The method of claim 7, wherein the one or more nanotubes have a defined length L, the surface wave has a defined frequency λ and wherein the ratio between L/λ is between about 10 and 25.

14. The method of claim 1, wherein the carbon nanotubes have a diameter between about 1 and 5 nm.

15. A method for nano-pumping, comprising the following steps:
   providing one or more carbon nanotubes, each carbon nanotube having a first end and a second end;
   imbibing the one or more carbon nanotubes with a media; and
   creating surface waves on the carbon nanotubes,
   wherein the one or more nanotubes have a defined length L, the surface wave has a defined frequency λ and wherein the ratio between L/λ is between about 2 and 32.

16. The method of claim 15, wherein the carbon nanotubes are open at both the first and second ends.

17. The method of claim 15, wherein the carbon nanotubes are capped at the first end and the open at the second end.

18. The method of claim 15, wherein the first end of the carbon nanotubes is in contact with the media.

19. The method of claim 15, wherein the media is a liquid, gas, solid or combination thereof.

20. The method of claim 15, wherein the surface waves have a frequency less than about 60 THz.

21. The method of claim 15, wherein the surface waves have a frequency between about 10 and 60 THz.

22. The method of claim 15, wherein the surface waves are created by sending ultrasound waves to the carbon nanotubes.

23. The method of claim 15, wherein the media is non-ionic.

24. The method of claim 15, wherein the maximum atomic flow rate of the media is between about 5 and 45 atoms/ps.

25. The method of claim 15, wherein the length of the one or more nanotubes is between about 10 nm and 100 nm.

26. The method of claim 15, wherein the maximum atomic axial velocity of the media is between about 2 and 35 km/s.

27. A method for nano-pumping, comprising the following steps:

providing one or more carbon nanotubes, each carbon nanotube having a first end and a second end;

imbibing the one or more carbon nanotubes with a media, wherein the media is hydrogen; and creating surface waves on the carbon nanotubes.

28. The method of claim 27, wherein the one or more nanotubes have a defined length L, the surface wave has a defined frequency $\lambda$ and wherein the ratio between L/$\lambda$ is between about 2 and 32.

29. The method of claim 27, wherein the one or more nanotubes have a defined length L, the surface wave has a defined frequency $\lambda$ and wherein the ratio between L/$\lambda$ is between about 10 and 25.

* * * * *